US00PP12577P2

(12) United States Plant Patent
Amorao et al.

(10) Patent No.: US PP12,577 P2
(45) Date of Patent: Apr. 23, 2002

(54) STRAWBERRY PLANT NAMED 'CANTERBURY'

(75) Inventors: Amado Q. Amorao, Camarillo; Arnoldo Solis, Jr., Oxnard; Thomas M. Sjulin, Aromas, all of CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 09/417,144

(22) Filed: Oct. 12, 1999

(51) Int. Cl.[7] ..... A01H 5/00
(52) U.S. Cl. ..... Plt./209
(58) Field of Search ..... Plt./208, 209

*Primary Examiner*—Bruce R. Campell
*Assistant Examiner*—Michelle Kizilkaya
(74) *Attorney, Agent, or Firm*—Pennie & Edmonds LLP

(57) ABSTRACT

This invention relates to a new and distinct variety of strawberry named 'Canterbury'. The variety is similar to the varieties 'Coronada' and 'San Miguel'. The variety is distinguished from 'Coronado' and 'San Miguel', in particular, by its upright to globose habit, very strong plant vigor, high density, obtuse shape of the terminal leaflet base, medium to dense petiole pubescence, its inflorescence being positioned level with the leaves, very slight to slight difference in the shapes of the primary and secondary fruits, absent or very weak unevenness of surface, strong sweetness, and fine texture when tasted.

2 Drawing Sheets

BACKGROUND OF THE INVENTION

The new variety originated as a result of a controlled cross between the strawberry plants '9A264' (unpatented variety) and 'Balboa' (U.S. Plant Pat. No. 9,130) in an ongoing breeding program, and was discovered as a seedling in a controlled breeding plot, in Ventura County, Calif. in February 1996. The original seedling of the new cultivar was asexually propagated by stolons in McArthur, Shasta County, Calif. 'Canterbury' was subsequently asexually propagated and underwent further testing in Ventura County, Calif. for three years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Canterbury'. The variety is botanically identified as *Fragaria×ananassa*. The new variety is distinguished from other varieties by a number of characteristics as set forth in Tables 1–6.

COMPARISON TO SIMILAR VARIETIES

The varieties which we believe to be similar to 'Canterbury' from those known to us are 'Coronado' (U.S. Plant Pat. No. 10,221) and 'San Miguel' (U.S. Plant Pat. No. 10,642). There are several characteristics of the new variety that are different from, or not possessed by 'Coronado' and 'San Miguel'. The new variety has an upright to globose habit, very strong plant vigor, high density, obtuse shape of the terminal leaflet base, medium to dense petiole pubescence, its inflorescence positioned level with the leaves, very slight to slight difference in the shapes of the primary and secondary fruits, absent or very weak unevenness of surface, strong sweetness, and fine texture when tasted.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
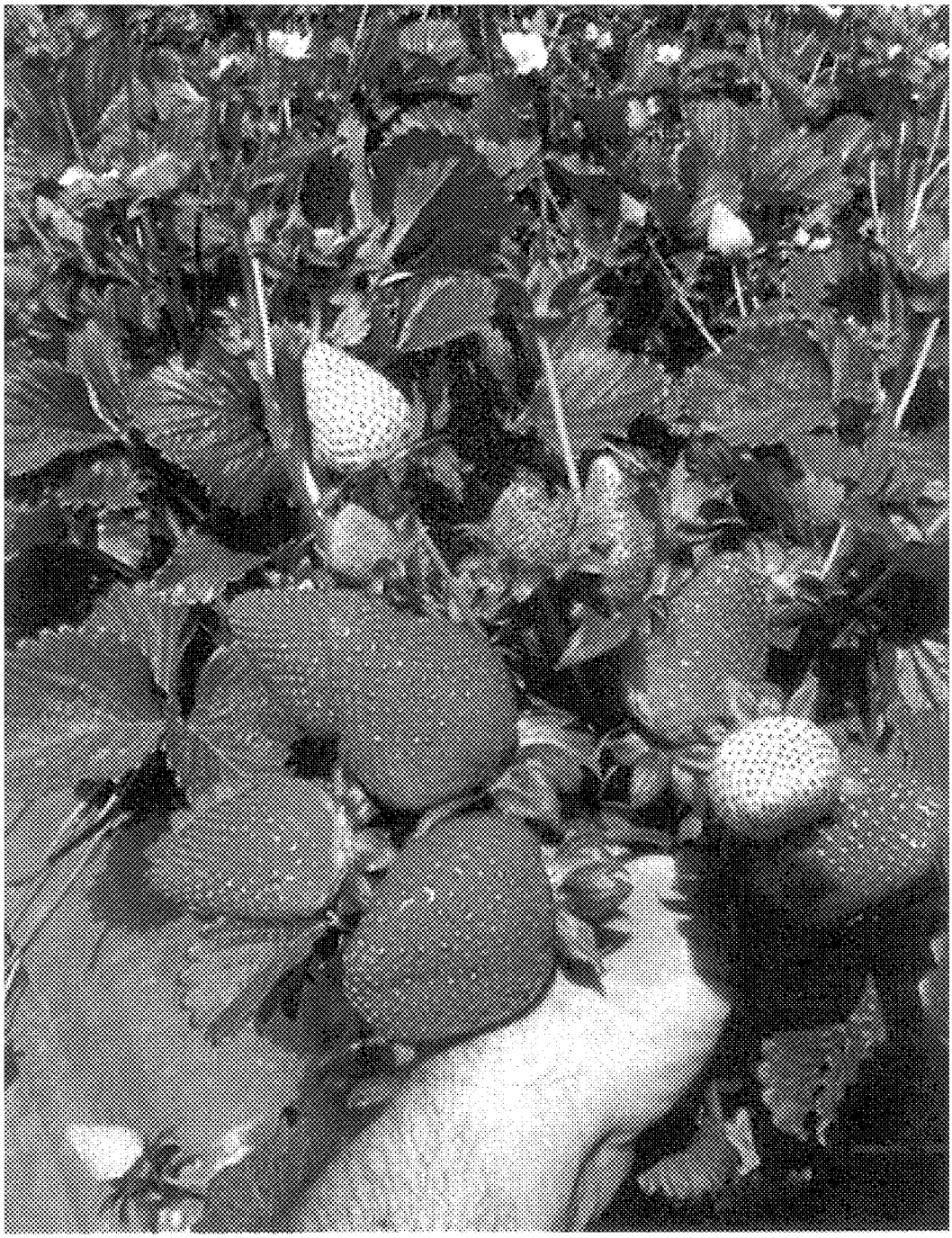
FIG. 1 shows the whole plant.
Figure 2:
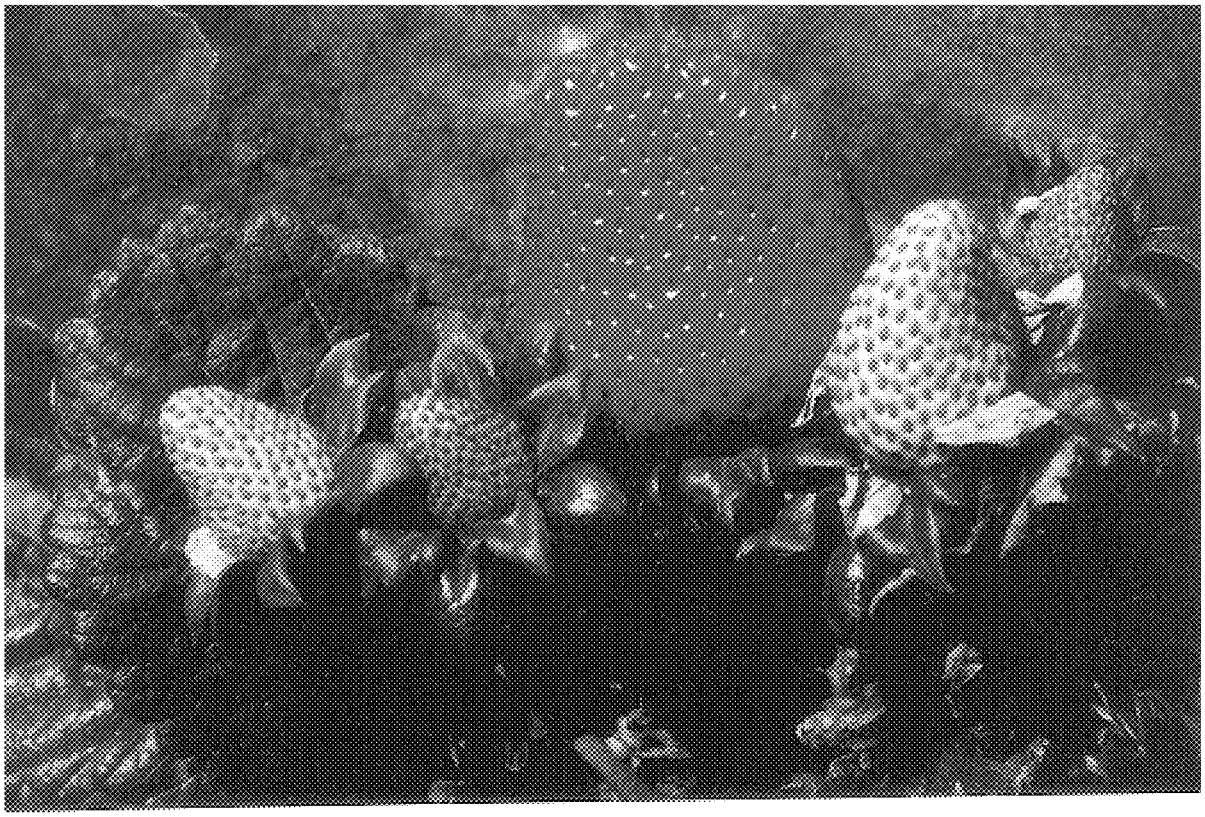
FIG. 2 shows typical whole fruit.

The following detailed description of the new variety is based upon observations taken of plants and fruit grown in Ventura County, Calif., U.S.A. Observations of 'Canterbury', 'Coronado' and 'San Miguel' were taken in side by side comparison in 1999. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2 and 3. In the tables, the flowers described are secondary flowers except where indicated. The petal color of 'Canterbury' is white which is not referenced in The R.H.S. Colour Chart. The fruit described is the secondary fruit on one year old plants. Fruit and flower measurements are an average of both primary and secondary fruit and flowers.

Table 1 provides information on the plant and fruit characteristics of the new variety 'Canterbury' compared with characteristics of 'Coronado' and 'San Miguel'. Table 2 provides additional information of the plant and fruit characteristics of the new variety 'Canterbury' compared with characteristics of the varieties 'Coronado' and 'San Miguel'. Table 3 provides reactions of the new variety to stresses as compared to the varieties 'Coronado' and 'San Miguel'. The average number of stamens is 29. Anthocyanin pigment on various plant origins is red to purple red in color. The average number of pedicels/peduncle is 5.6. The average diameter of a peduncle is 5.4 mm. The average length of a peduncle is 24.9 cm. The average pedicel diameter is 1.9 mm. The average length of the pedicels is 9.8 cm. The average petiole diameter is 4.1 mm. Achene color is red to yellow-green (46A to 151B). The average sepal number is 11.3 and average sepal size is 1.05 cm. Typical sugar content, as measured by total soluble solids, is 9.5% to 10.5%. An abundant amount of pollen produced. Tables 4 and 5 provide information of the new variety's reaction to pests and diseases, respectively, compared to the varieties 'Coronado' and 'San Miguel'. Table 6 provides isozyme characteristics of the new variety as compared to the varieties 'Coronado' and 'San Miguel'.

TABLE 1

DETAILED COMPARISON OF 'CANTERBURY', 'CORONADO', AND 'SAN MIGUEL'

| | Canterbury | Coronado | San Miguel |
|---|---|---|---|
| Plant Characteristics | | | |
| Height of Plant (cm) | 30.2 | 39.8 | 30.3 |
| Spread of Plant (cm) | 43.6 | 42.2 | 37.2 |
| Number of Crowns | 4.9 | 4.5 | 3.1 |
| Leaf Characteristics | | | |
| Terminal Leaflet Width (cm) | 9.1 | 7.7 | 7.9 |
| Terminal Leaflet Length (cm) | 8.8 | 8.5 | 7.3 |
| Terminal Leaflet Length/Width Ratio | 0.97 | 1.1 | 0.93 |
| Number of Teeth/Terminal Leaflet | 24.7 | 20.1 | 22.7 |
| Petiole Length (cm) | 16.7 | 22.0 | 22.6 |
| Bract Frequency | 0% Typically Single | 10% Typically single | 10% Typically Single |
| Stipule Length (cm) | 3.3 | 3.9 | 3.7 |
| Stipule Width (cm) | 1.1 | 1.3 | 1.0 |
| Flower Characteristics | | | |
| Petal Width (cm) | 1.5 | 1.6 | 1.6 |
| Petal Length (cm) | 1.6 | 1.7 | 1.6 |
| Petal Length/Width Ratio | 0.95 | 0.95 | 0.98 |
| Flower Diameter (cm) | 3.7 | 4.2 | 4.1 |
| Calyx Diameter (cm) | 4.6 | 6.0 | 4.9 |
| Fruit Characteristics | | | |
| Fruit Width (cm) | 4.2 | 4.4 | 4.4 |
| Fruit Length (cm) | 4.8 | 4.8 | 5.1 |
| Fruit Length/Width Ratio | 1.14 | 1.09 | 1.16 |
| Average Berry Size (g) | 20.7 | 23.8 | 25.3 |
| Fruit Skin Color | Orange red 46A | Dark red 46A | Dark red 46A |
| Fruit Flesh Color | Red 42A | Orange red 43A | Dark red 45B |
| Total Yield (g/plant) | 522 | 526 | 482 |

TABLE 2

CHARACTERISTICS OF 'CATERBURY', 'CORONADO', AND 'SAN MIGUEL'

| | Canterbury | Coronado | San Miguel |
|---|---|---|---|
| Plant | | | |
| Habit | upright to globose | flat globose | globose to flat globose |
| Density | dense | open to medium | open |
| Vigor | very strong | strong | medium to strong |
| Leaf | | | |
| Color of upper side | Green 137A | Dark Green 147A | Green 137A |
| Color of under side | Light grey green 138C | Light grey green 147C | Light grey green 138C |
| Shape in cross section | concave | concave | concave |
| Interveinal blistering | strong | medium strong | strong |
| Glossiness | weak | weak | weak to medium |
| Number of leaflets | 3 on 90% of leaves; 4 on 10% of leaves | 3 | 3 |
| Terminal leaflet margin profile | flat | flat | revolute to flat |
| Terminal leaflet shape of base | obtuse | obtuse to rounded | rounded |
| Terminal leaflet shape of teeth | obtuse | obtuse | obtuse |
| Petiole pubescence | medium to dense | medium | medium |
| Petiole pose of hairs | upwards to outwards | upwards | upwards to outwards |
| Stolon | | | |
| Number | medium to many | medium | many |
| Anthocyanin coloration | weak to medium | strong | strong |
| Thickness | medium | thin | thin to medium |
| Pubescence | medium | sparse | sparse to medium |
| Inflorescence | | | |
| Position relative to foliage | level | above | above |
| Diameter of calyx relative to corolla | same size to larger | same size to larger | smaller |
| Diameter of inner calyx relative to outer | same size to larger | larger | same size to larger |
| Spacing of petals | overlapping | overlapping | touching to overlapping |
| Fruiting Truss | | | |
| Attitude at first picking | erect | semi-erect to prostrate | prostrate |
| Length (cm) | 16.4 | 28.6 | 25.3 |

TABLE 2-continued

CHARACTERISTICS OF 'CATERBURY', 'CORONADO', AND 'SAN MIGUEL'

| | Canterbury | Coronado | San Miguel |
|---|---|---|---|
| Fruit | | | |
| Predominant shape | conical to cordate | conical to almost cylindrical | conical to cordate |
| Difference in shapes between primary and secondary fruits | very slight to slight | moderate | marked |
| Band without achenes | absent or very narrow | narrow | narrow to medium |
| Unevenness of surface | absent or very weak | weak to medium | medium |
| Evenness of color | even | even | even |
| Glossiness | medium | strong | medium to strong |
| Insertion of achenes | level with surface | level with surface | level with surface |
| Insertion of calyx | level | in a basin to level | set above |
| Pose of the calyx segments | spreading to reflexed | spreading to reflexed | reflexed |
| Size of calyx in relation to fruit | larger | larger | same size to larger |
| Firmness of flesh | medium to firm | firm | medium to firm |
| Evenness of flesh color | slightly eneven | slightly uneven | slightly uneven |
| Distribution of flesh color | marginal and central | marginal and central | marginal and central |
| Hollow center size | small to medium | small to medium | small to medium |
| Sweetness | strong | weak | medium |
| Texture when tasted | fine | fine to medium | medium |
| Acidity | weak | strong | strong |
| Time of Flowering | early | early to medium | early |
| Time of Fruiting | early | early to medium | early |
| Time of Bearing | partially everbearing | partially everbearing | partially everbearing |

REACTION TO STRESS

TABLE 3

| | Canterbury | Coronado | San Miguel |
|---|---|---|---|
| Reaction to Stress | | | |
| high pH | Moderately Resistant | Moderately Resistant | Moderately Resistant |
| high soil salt levels | Moderately Resistant | Moderately Resistant | Moderately Resistant |

PEST AND DISEASE RESISTANCE AND SUSCEPTIBILITY

TABLE 4

| | Canterbury | Coronado | San Miguel |
|---|---|---|---|
| Reaction to Pests | | | |
| *Tetranychus urticae* | susceptible | susceptible | susceptible |
| Aphis spp. | susceptible | susceptible | susceptible |
| *Lygus hesperus* | susceptible | susceptible | susceptible |

TABLE 5

| | Canterbury | Coronado | San Miguel |
|---|---|---|---|
| Reaction to Diseases | | | |
| Bortrytis fruit rot | moderately resistant | susceptible | highly susceptible |
| Powdery mildew | moderately resistant | moderately resistant | moderately resistant |
| Verticillium wilt | highly susceptible | susceptible | highly susceptible |
| Strawberry Mottle Virus | moderately resistant | moderately resistant | moderately resistant |
| Xanthomonas fragariae | susceptible | susceptible | susceptible |

ISOZYME ANALYSIS

In addition to the morphological description above, the new cultivar 'Canterbury' has been analyzed to obtain an indication of its genetic makeup to provide further means for identifying the new variety and distinguishing it from some other somewhat similar and/or related strawberry varieties. Specifically, leaf samples of 'Canterbury', 'Coronado', and 'San Miguel' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the three varieties is presented in Table 4, with the letters representing the banding patterns for each enzyme as designated in the above-identified article.

TABLE 6

ISOZYME ANALYSIS FOR 'CANTERBURY', 'CORONADO', AND 'SAN MIGUEL'

| Locus | Canterbury | Coronado | San Miguel |
|---|---|---|---|
| PGI | A3 | A2 | A4 |
| LAP | B3 | B3 | B3 |
| PGM | C3 | C4 | C2 |

What is claimed is:

1. A new and distinct variety of strawberry plant, substantially as shown and described.

* * * * *